(12) United States Patent
Morren

(10) Patent No.: US 8,563,946 B2
(45) Date of Patent: Oct. 22, 2013

(54) OLED PHOTOTHERAPY DEVICE

(75) Inventor: Geert Guy Georges Morren, Vissenaken (BE)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 13/375,280

(22) PCT Filed: Jun. 17, 2010

(86) PCT No.: PCT/IB2010/052735
§ 371 (c)(1),
(2), (4) Date: Nov. 30, 2011

(87) PCT Pub. No.: WO2011/004277
PCT Pub. Date: Jan. 13, 2011

(65) Prior Publication Data
US 2012/0104277 A1    May 3, 2012

Related U.S. Application Data

(60) Provisional application No. 61/224,120, filed on Jul. 9, 2009.

(51) Int. Cl.
*B01J 19/12* (2006.01)

(52) U.S. Cl.
USPC ............................ 250/455.11; 607/88; 607/90

(58) Field of Classification Search
USPC .................................................... 250/455.11
See application file for complete search history.

(56) References Cited

U.S. PATENT DOCUMENTS

| | | | |
|---|---|---|---|
| 3,877,437 A * | 4/1975 | Maitan et al. | 607/91 |
| 4,509,505 A | 4/1985 | Mercey et al. | |
| 5,119,467 A | 6/1992 | Barsky et al. | |
| 5,285,519 A | 2/1994 | Barsky et al. | |
| 6,596,016 B1 | 7/2003 | Vreman et al. | |
| 6,866,678 B2 * | 3/2005 | Shenderova et al. | 607/88 |
| 7,008,371 B2 * | 3/2006 | Goldberg et al. | 600/22 |
| 7,131,990 B2 * | 11/2006 | Bansal et al. | 607/90 |
| 2007/0027510 A1 | 2/2007 | Rodrigues et al. | |

FOREIGN PATENT DOCUMENTS

| | | |
|---|---|---|
| WO | 2005123189 A2 | 12/2005 |
| WO | 2007091188 A1 | 8/2007 |
| WO | 2009050213 A1 | 4/2009 |
| WO | 2009073396 A1 | 6/2009 |

* cited by examiner

*Primary Examiner* — Phillip A Johnston
(74) *Attorney, Agent, or Firm* — Timothy A. Nathan

(57) ABSTRACT

The invention provides a phototherapy device that includes a controlled environment defined by a plurality of transparent panels and at least one light emitting diode portion that projects light into the controlled environment.

20 Claims, 7 Drawing Sheets

OLED PHOTOTHERAPY DEVICE

The invention relates to an incubator-based phototherapy device for infants or other patients.

By some measurements, 60% of normal newborns suffer from jaundice (hyperbilirubinemia) during the first week of life. Although most newborns with jaundice are otherwise healthy, they must be monitored and treated, if necessary, because bilirubin is potentially toxic to the central nervous system.

Phototherapy is the standard of care for the treatment of neonatal jaundice. Phototherapy lowers the concentration of serum bilirubin by using light energy to change the shape and structure of bilirubin, converting it to molecules that can be excreted. The efficacy of phototherapy is mainly determined by the spectrum and the intensity of the light.

In some instances, phototherapy is delivered to a patient via an incubator that delivers light to the patient via a light unit mounted on a stand that is positioned over the incubator. However, these existing systems require a bulky external light unit. The light unit occupies a large amount of space and presents workflow-related obstacles. Other inefficiencies also exist with phototherapy treatment devices.

The present disclosure relates to an apparatus for providing phototherapy to a patient utilizing an enclosure and an illumination portion that includes organic light emitting diodes (OLEDs). The enclosure may define an environment and/or receiving space for receiving and/or enclosing a patient such as, for example an human infant. The OLEDs may project light into the controlled environment/receiving space.

The enclosure may include a top portion, a bottom portion and multiple side portions, each of which may connect the top portion and the bottom portion. In some implementations, one or more of the top, bottom, and/or side portions of the enclosure may include one or more panels. In some implementations, one or more of the panels may be transparent panels. In some implementations, the panels or other portions of the enclosure desired to be transparent may be constructed of, for example, glass, acrylic glass (e.g., Plexiglas), and/or other transparent material.

In some implementations, the enclosure may include one or more openings therein that provide access to the controlled environment and/or any patient placed therein. In some implementations, one or more portions/panels of the enclosure may be movable (e.g., removable, hinged to another portion/panel, etc.) so that a patient (e.g., an infant) may be placed within and removed from the controlled environment/receiving space.

The illumination portion of the apparatus projects light into the controlled environment/receiving space. As discussed herein, the illumination portion may comprise a panel including an organic light emitting diode (OLED) that emits light when energized. In some implementations, the OLEDs used to project light for phototherapy may be transparent when not energized. The organic light emitting diode may include several layers and any associated electrical components.

In some implementations, the illumination portion may project light having a wavelength of between 400 nm and 550 nm into the controlled environment. A wavelength of between 400 nm-550 nm may be used because this range may be effective in the treatment of jaundice in a patient. In some implementations, however, light having other wavelengths or ranges thereof may be used.

In some implementations, the illumination portion may project light into the controlled environment providing an irradiance in the range of 10-35 microWatt/cm$^2$/nm. The irradiance range of 10-35 microWatt/cm$^2$/nm may provide the desired irradiance for treatment of jaundice in a patient. However, other irradiances or ranges thereof may be used.

In some implementations, the illumination portion may project light into the controlled environment at an intensity of between 1500 Lm and 2000 Lm. However, other intensities or ranges thereof may be used.

In some implementations, a single OLED panel may be used as an illumination portion. In some implementations, to achieve a desired intensity of light for phototherapy, OLED panels used for illumination portions of the invention maybe required to have a certain surface area. This may depend on the intensity of light achieved by a given type of OLED technology. For example, in some instances, 0.5 m$^2$ of OLED surface area may be needed to achieve an intensity of 1500-2000 Lm. In some implementations, multiple OLED panels may be needed to achieve a desired intensity of light. Multiple OLED panels maybe used for other purposes as well.

In some implementations, the OLED panels may be attached to the top portion of the enclosure. In some implementations, OLED panels may be placed on portions of the enclosure other than the top portion (e.g., bottom and/or side portions).

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
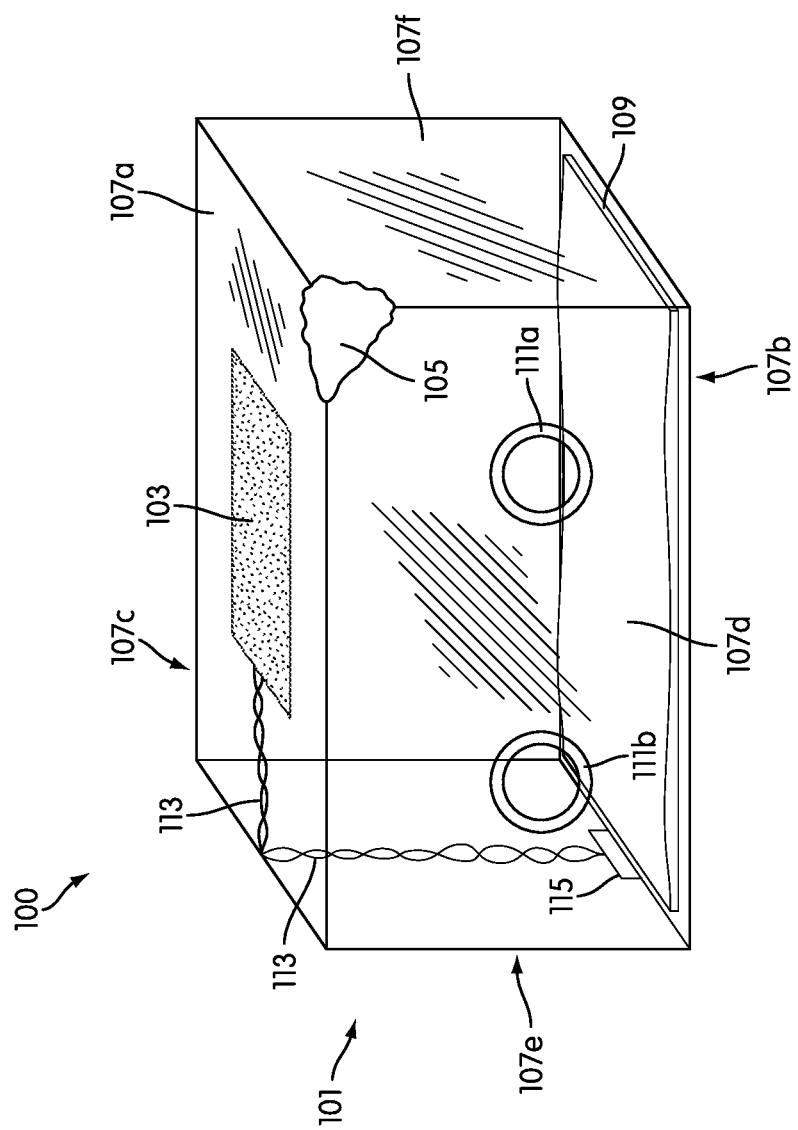
FIG. 1 is an example of a phototherapy device according to various implementations of the invention.

One aspect of the invention provides an apparatus for providing phototherapy to a patient utilizing an enclosure and organic light emitting diodes. FIG. 1 illustrates a phototherapy apparatus 100 according to various implementations of the invention. Phototherapy apparatus 100 includes an enclosure 101 and an illumination portion 103. Enclosure 101 defines an environment and/or receiving space 105 for receiving and/or enclosing a patient such as, for example, an human infant. Illumination portion 103 projects light into controlled environment/receiving space 105.

Figure 2A:
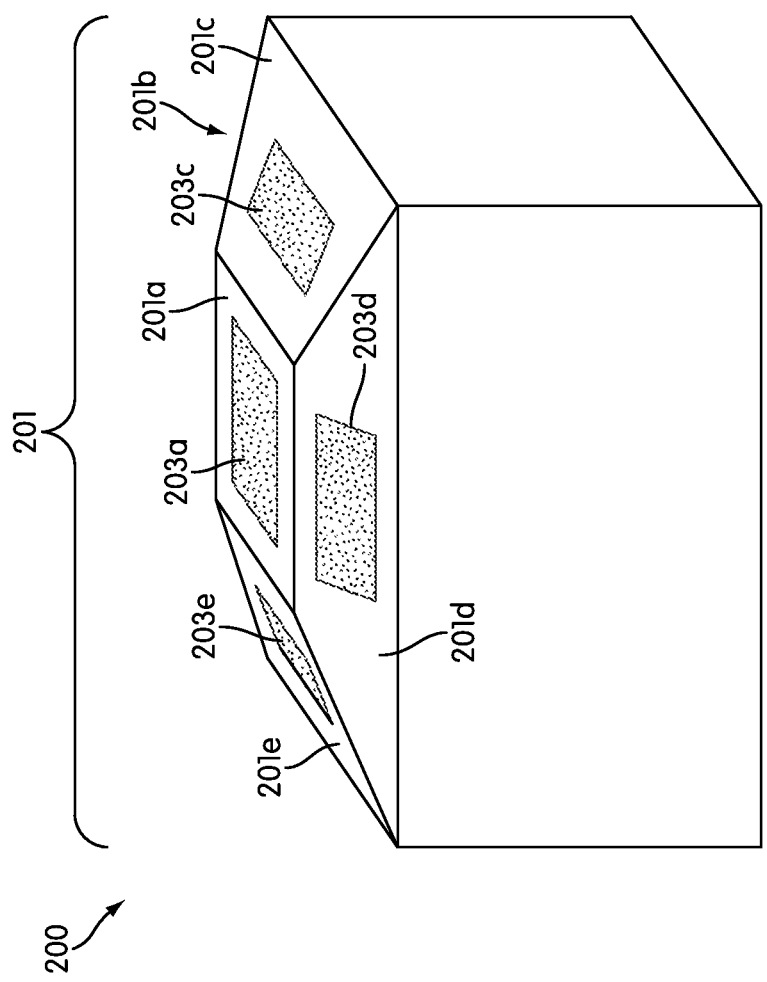
FIG. 2A is an example of a phototherapy device according to various implementations of the invention.
Figure 2B:
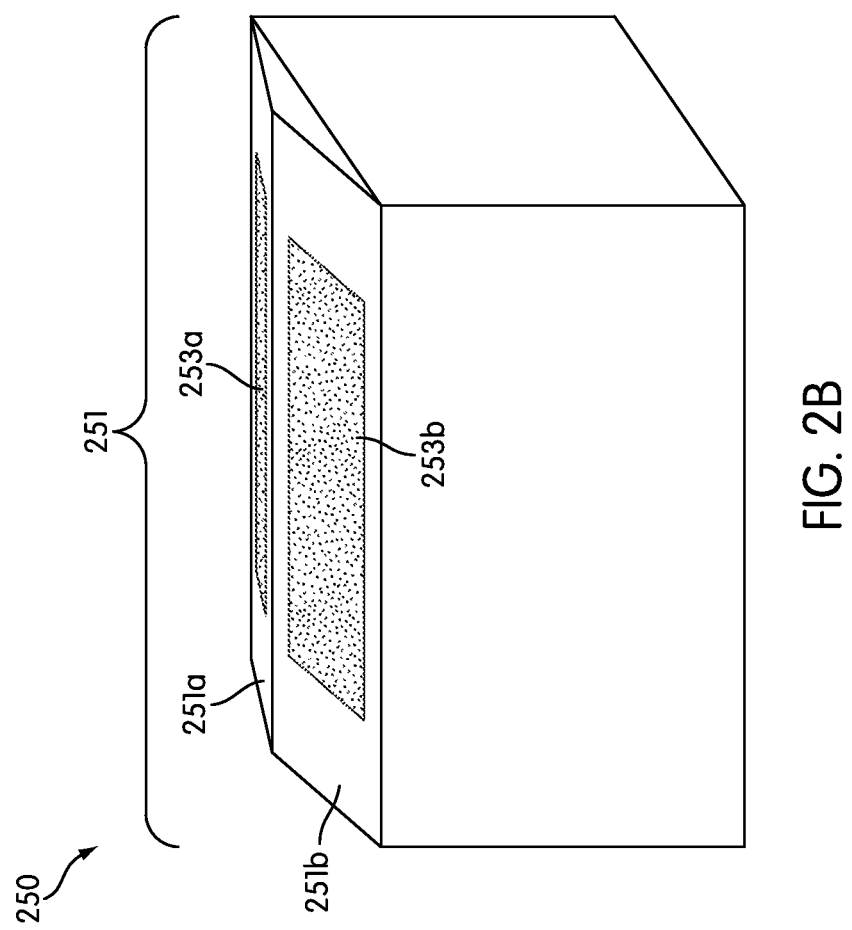
FIG. 2B is an example of a phototherapy device according to various implementations of the invention.

Enclosure 100 may include a top portion 107a and a bottom portion 107b (i.e., the underside of enclosure 101 as illustrated in FIG. 1). In some implementations, top portion 107a may include a top panel that is parallel to bottom portion 107b. In some implementations, top portion 101a may include multiple panels. For example, FIG. 2A illustrates an phototherapy apparatus 200 according to various embodiments of the invention wherein top portion 201 includes multiple panels 201a-201e (panel 201b being obscured in FIG. 2A). As illustrated in FIG. 2A, only panel 201a is parallel to bottom portion 203, however, in some implementations, none of the panels of the top portion of an enclosure according to the invention need be parallel to the bottom portion of such an enclosure. For example, FIG. 2B illustrates a phototherapy apparatus 250 according to various embodiments of the invention wherein top portion 251 includes panels 251a-251b, neither of which are parallel to the bottom portion (not illustrated). The present invention also contemplates that the enclosure can have any shape suitable to receive the patient.

Returning to FIG. 1, in some implementations, bottom portion 107b may include a bottom panel. In some implementations, a cushion 109 or other elements on which a patient may be placed may exist within the controlled environment on a top surface of bottom portion 107b.

Enclosure 101 may include side portions 107c (i.e., the back panel in FIG. 1), 107d (i.e., the front panel in FIG. 1), 107e (i.e., the left-hand panel in FIG. 1), and 107f (i.e., the right-hand panel in FIG. 1), each of which may connect top portion 107a and bottom portion 107b. In some implementations, each of side portions 107c, 107d, 107e, and 107f may include flat panels. In some implementations, one or more of portions 107c, 107d, 107e, and/or 107f may include multiple panels. In some implementations, some side portions may be longer than others (e.g., side portions 107c and 107d may be longer than side portions 107e and 107O so that the enclosure forms a rectangular shape when viewed from above. In some implementations, the enclosure may form other shapes when viewed from this or other perspectives by virtue of portions of enclosure having different sizes/shapes.

In some implementations, one or more of the plurality of panels 107 of enclosure 101 may be transparent panels. In some implementations all of the panels may be transparent such that enclosure 101 is generally a transparent enclosure. In some implementations, the panels or other portions of enclosure 101 desired to be transparent may be constructed of, for example, glass, acrylic glass (e.g., Plexiglas), and/or other transparent material.

Figure 5:
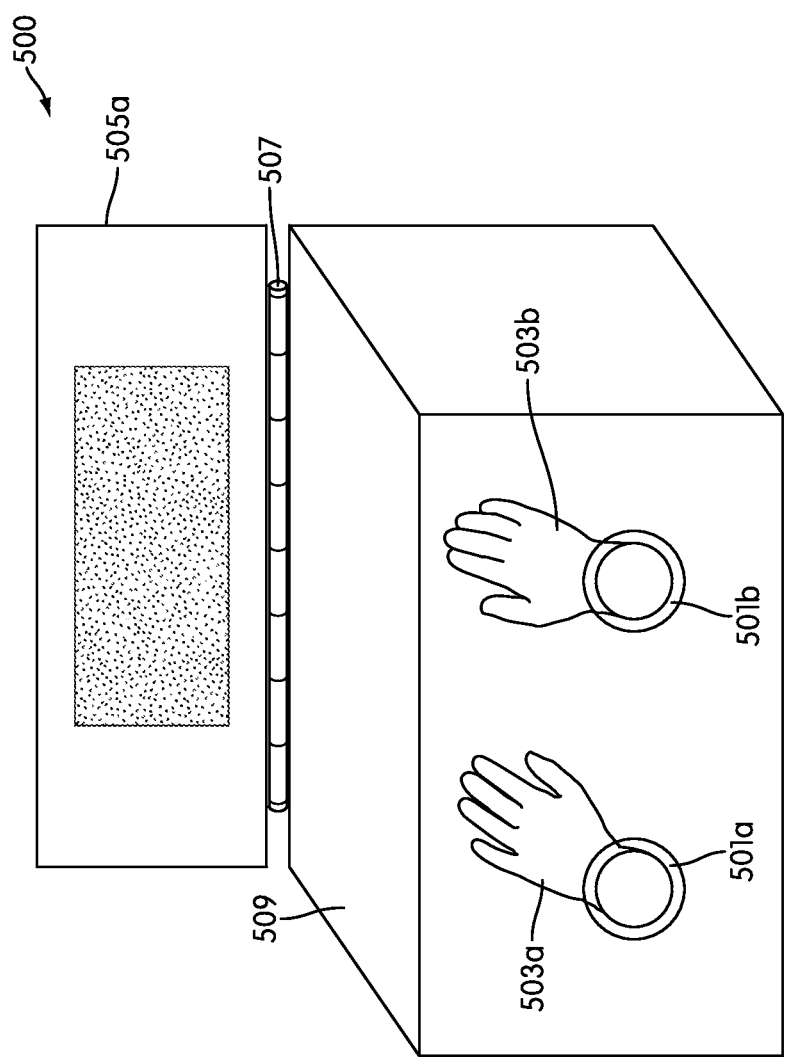
FIG. 5 is an example of a phototherapy device according to various implementations of the invention.

In some implementations, enclosure 101 may include one or more openings therein that provide access to the controlled environment and/or any patient placed therein. For example, FIG. 1 illustrates that side portion 107d may include openings 111a and 111b. In some implementations, openings in an enclosure portion may be provided with integrally formed gloves that extend into the enclosure as known in the art. For example, FIG. 5 illustrates a phototherapy device 500, having openings 501a and 501b. Associated with 501a and 501b are gloves 503a and 503b respectively, so that a user (e.g., medical professional, parent, caregiver, etc.) may access and/or manipulate items in the controlled environment (e.g., an infant and any associated clothing and/or devices) without contaminating the items and/or the controlled environment (i.e., the open portions of gloves 503a and 503b are sealed to openings 501a and 501b, respectively, so that the skin of the hands of the user are not exposed to the controlled environment).

In some implementations, one or more portions/panels of enclosure 101 may be movable (e.g., removable, hinged to another portion/panel, etc.) so that a patient (e.g., an infant) may be placed within and removed from controlled environment 105. For example, the top panel 107a may be connected to any side panel (e.g., panels 107c, 107d, 107e or 107f) by one or more hinges, for example. FIG. 5 illustrates a phototherapy device 500 which may include a top portion 505a that is connected to a back portion (obscured in FIG. 5) by a hinge 507 so that an opening 509 may be provided to place an infant and/or any associated implements (e.g., medical equipment or parts thereof) into (and removed from) the controlled environment.

Illumination portion 103 projects light into controlled environment 105. In some implementations, illumination portion 105 may comprise at least one organic light emitting diode (OLED) panel that emits light when energized. Illumination portion 103 may include lead wires 113, which may provide power to the at least one OLED panel. In some implementations, lead wires 113 may connect the at least one OLED panel to a connector 115, which may provide an electrical coupling from a power source (e.g., an AC electrical outlet, a battery or other DC power source, or other power source) so as to energize the at least one OLED panel. In some implementations, illumination portion 103 may include a switch (not illustrated) so as to selectively energize and de-energize the at least one OLED panel. In implementations wherein multiple OLED panels are used, each of the multiple OLED panels may include a separate switch or other mechanism for energizing/de-energizing the OLED panel so that each OLED panel may be separately energized/de-energized.

Figure 3:
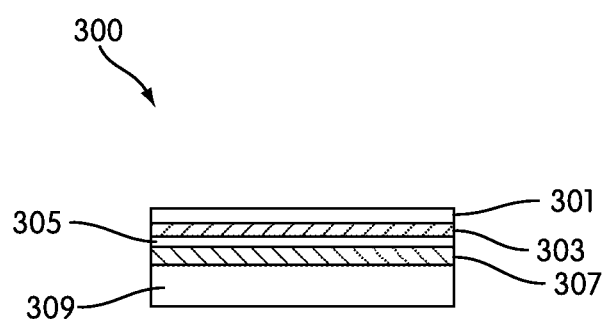
FIG. 3 is an example of an organic light emitting device according to various implementations of the invention.

The quantity and spacing of the OLEDs may vary and the present invention is not limited in this respect. In some implementations, the OLEDs used to project light for phototherapy may be transparent when not energized (i.e., the component layers of the OLEDs may each be transparent when the OLED is not energized). The organic light emitting diode may include several layers and any associated electrical components. FIG. 3 illustrates an example of an OLED 300 according to an embodiment of the invention. OLED 300 is not drawn to scale relative to the other figures of this document. OLED 300 may include multiple layers such as, for example, a cathode 301, an emissive layer 303 (which may include organic molecules or polymers), a conductive layer 305 (which may include organic molecules or polymers), an anode 307, a substrate 309 (e.g., glass), and/or other layers or components. OLED's used in phototherapy devices according to the invention may also include any necessary or desired wiring, power sources, and/or other components necessary to produce light.

In some implementations, illumination portion 103 may project light having a wavelength of between 400 nm and 550 nm into controlled environment 105. A wavelength of between 400 nm-550 nm may be used because this range may be effective in the treatment of jaundice in a patient. In some implementations, however, light having other wavelengths or ranges thereof may be used.

In some implementations, the illumination portion may project light into the controlled environment providing an irradiance in the range of 10-35 microWatt/cm$^2$/nm. The irradiance range of 10-35 micro-Watt/cm$^2$/nm may provide the desired irradiance for treatment of jaundice in a patient. However, other irradiances or ranges thereof may be used.

In some implementations, illumination portion 103 may project light into controlled environment 105 at an intensity of between 1500 Lm and 2000 Lm. However, other intensities or ranges thereof may be used.

In some implementations, a single OLED panel may be used as an illumination portion. For example, FIG. 1 illustrates that a single panel is used as illumination portion 103 and is attached to top portion 107a. The OLED panel of illumination portion 103 includes at least one light-emitting surface. In some implementations, the OLED panel may include two surfaces that emit at least some light, however, one of the surfaces may be a primary light emitting surface and one may be considered a "dark" surface (even though the surface may emit some level of light). In some implementations, the dark surface (or non-primary-light-emitting surface) may not emit any light. In some implementations, the dark surface of the OLED panel may be mounted to an inner surface of a panel of enclosure 101 (e.g., panel 107a as illustrated in FIG. 1) so that the light-emitting surface of the OLED panel is directly exposed to the controlled environment and therefore light is projected directly from the OLED panel into controlled environment 105.

In some implementations, particularly those wherein at least one portion of enclosure 101 is made from a transparent material, the light-emitting surface of an OLED panel may be mounted on an outer surface of the at least one transparent portion of enclosure 101 (e.g., panel 107a as illustrated in FIG. 1) so that the light projected from the OLED panel must pass completely through the at least one transparent portion before entering controlled environment 105. Mounting the OLED panel on the outer surface of enclosure may provide the advantage of easy removal and replacement of the OLED panel (e.g., for replacing damaged OLED panels). Of course, mounting the OLED panel on an inner surface of enclosure 101 may provide similar ease of convenience if the inner surface is easily accessible (e.g., hinged to another portion of enclosure 101).

Figure 6:
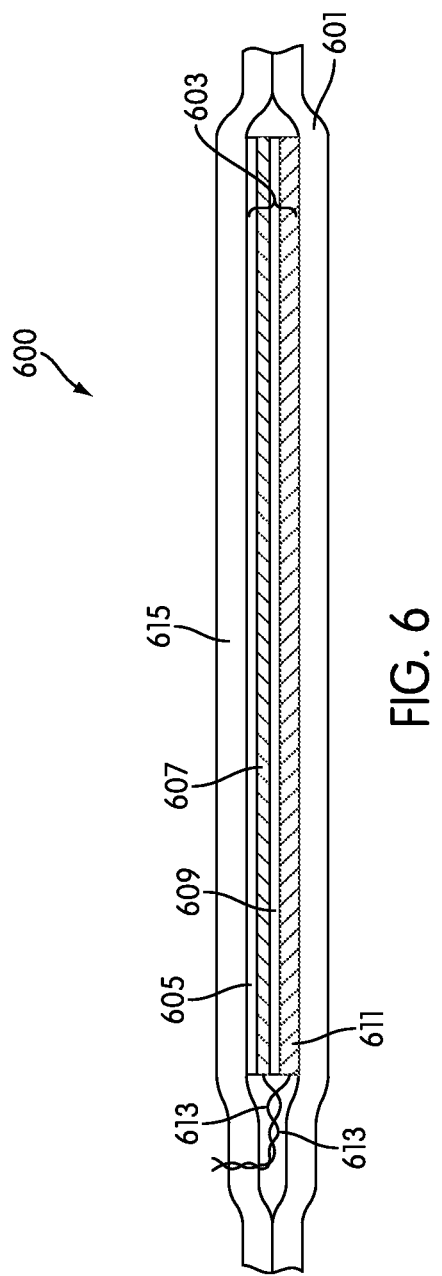
FIG. 6 illustrates an example of a cross-section of a panel having an OLED device therein, according to various implementations of the invention.

In some implementations, an OLED panel may be embedded within or integrated within a layer of or in between layers of a portion of enclosure 101 (e.g., panel 107a as illustrated in FIG. 1) such that light from a light-emitting surface of the OLED panel of illumination portion 103 must pass through a portion of enclosure 101 before entering into controlled environment 105. FIG. 6 illustrates a cross-section of a panel 600 of an enclosure of a phototherapy device according to various implementations of the invention. Panel 600 is not drawn to scale relative to the other figures of this document. Panel 600 includes an inner portion 601, which is a transparent material (e.g., glass, acrylic glass, etc.) and which may serve as a substrate for OLED panel 603. OLED panel 603 may include anode 605, a conductive layer 607, an emissive layer 609, a cathode 611, and lead wires 613 (which may service to complete the circuit of OLED 603). Panel 600 may also include an outer portion 615, which may also be a transparent material. In some implementations, an OLED panel integrated into an enclosure may have a substrate separate from the enclosure itself. This may make replacing or adjusting the OLED panel more convenient and/or cost effective.

Thus, it is contemplated that in some implementations the illumination portion 103 may be integrated with and form part of one of the panels (e.g., top panel 107a). In some implementations, the illumination portion may be a separate unit placed on top of one of the panels (e.g., on top of panel 107a), or mounted on the inner surface of one of the panels (e.g., mounted on the undersurface of top panel 107a). Such mounting of a separate illumination portion 103 may be accomplished by an adhesive connection, bolts, screws, fasteners, and/or other connection. For any of these embodiments, whether the illumination portion 103 is integrally formed with a panel of the enclosure or formed separately and then joined to the enclosure, it can be considered that the illumination portion 103 is provided "on" the enclosure 101.

In some implementations, to achieve a desired intensity of light for phototherapy, OLED panels used for illumination portions of the invention maybe required to have a certain surface area. This may depend on the intensity of light achieved by a given type of OLED technology. For example, in some instances, 0.5 m$^2$ of OLED surface area may be needed to achieve an intensity of 1500-2000 Lm. In some implementations, multiple OLED panels may be needed to achieve a desired intensity of light. Multiple OLED panels maybe used for other purposes as well. While FIG. 1 illustrates one OLED panel, multiple OLED panels may be spaced along top portion 107a. FIG. 2A illustrates that illumination portion 203 of phototherapy apparatus 200 includes OLED panels 203a-203e (OLED panel 203b being obscured and thus not labeled in FIG. 2A). FIG. 2B illustrates that illumination portion 253 of phototherapy apparatus 250 includes OLED panels 253a and 253b.

Figure 4:
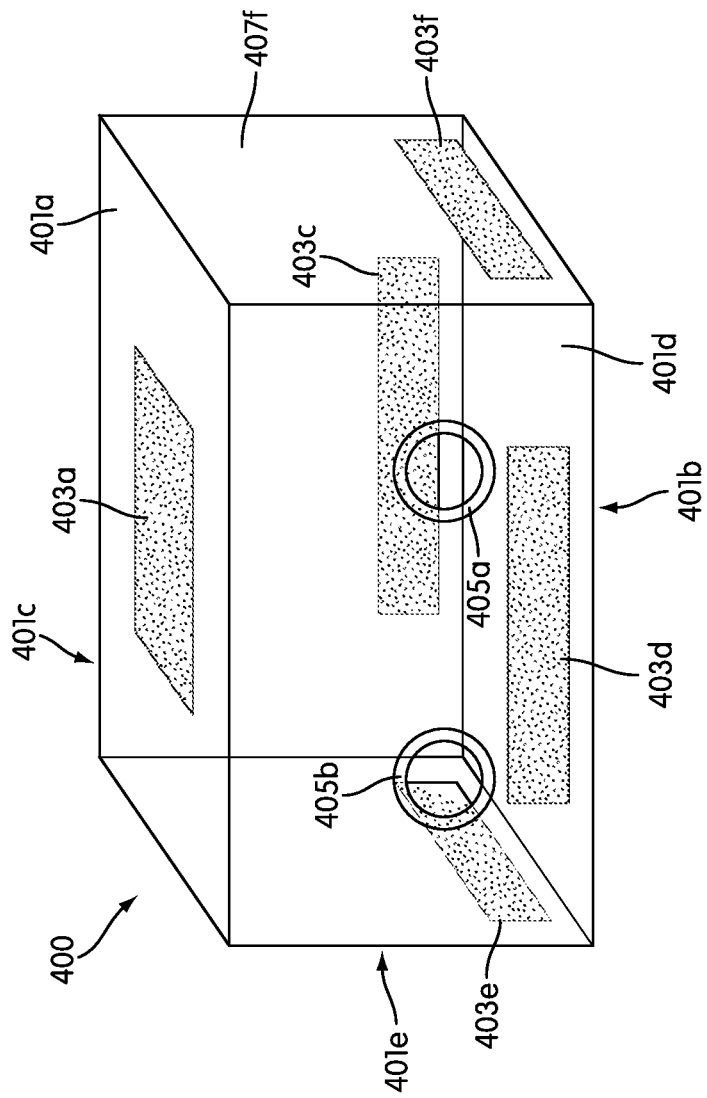
FIG. 4 is an example of a phototherapy device according to various implementations of the invention.

In some implementations, OLED panels may be placed on portions of enclosure 101 other than the top portion. In one example, location of an OLED panel on bottom portion 107b may expose a greater surface area of the patient's skin to light, thereby increasing effectiveness of treatment. In some implementations, one or more portions of enclosure 101 (e.g., portions 107a-107f) may include surfaced angled and/or oriented to better project light from one or more OLED panels onto a patient. FIG. 4 illustrates a phototherapy apparatus 400, wherein illumination portion 403a includes a first OLED panel 403a mounted on a top portion 401a of enclosure 401 and additional OLED panels 403c-403f mounted on side portions 401c-401f toward bottom portion 401b. Locating the additional OLED panels in this position provides greater light exposure to the patient and avoids interference with placement of access openings 405a-405b.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A phototherapy device, comprising:
   an enclosure portion enclosing a receiving space that is configured to receive an infant, the enclosure portion at least partially comprising a transparent material; and
   at least one illumination portion attached to the enclosure portion, the illumination portion comprising at least one light emitting diode portion that projects light having a wavelength between 400 nm and 550 nm and having an irradiance of between 10 microWatt/cm2/nm and 35 microWatt/cm2/nm when energized,
   wherein the enclosure portion is formed by a plurality of panels that are contiguous to one another, the plurality of panels including a first panel that serves as a substrate for an anode layer and a cathode layer of the at least one illumination portion, the first panel being formed from a transparent material such that the receiving space is exposed to ambient light through the first panel.

2. The phototherapy device of claim 1, wherein the enclosure portion includes at least one opening having at least one glove portion attached thereto such that a user is able to manipulate one or more objects in the receiving space using the at least one glove portion.

3. The phototherapy device of claim 1, wherein at least a portion of the enclosure portion is movable so as to provide an opening through which the infant is moved such that the infant is able to be placed in and removed from the receiving space.

4. The phototherapy device of claim 1, wherein the at least one light emitting diode portion is transparent when not energized such that the receiving space is exposed to ambient light through the light emitting diode portion.

5. The phototherapy device of claim 1, wherein the enclosure portion includes a top portion, a bottom portion arranged parallel to the top portion and four side portions, the four side portions comprising two long side portions arranged parallel to one another and two short side portions arranged parallel to one another.

6. The phototherapy device of claim 1, wherein the at least one illumination portion is on an outer surface of the enclosure portion.

7. The phototherapy device of claim 1, wherein the illumination portion has at least one light-emitting surface that projects the light into the receiving space, and wherein the at least one illumination portion is integrated into a portion of the enclosure such that at least the light-emitting surface of the illumination portion is covered by the transparent material of the enclosure portion.

8. The phototherapy device of claim 1, wherein the illumination portion has at least one light emitting surface that projects the light into the receiving space, wherein the illumination portion is attached to an inner surface of the enclosure portion.

9. The phototherapy device of claim 5, wherein the illumination portion comprises two or more light emitting diode portions, wherein at least a first light emitting diode portion is attached to the top portion of the enclosure portion and at least a second light emitting diode portion is attached to bottom portion of the enclosure portion.

10. The phototherapy device of claim 1, wherein the at least one light emitting diode portion includes an organic light emitting diode portion.

11. A phototherapy device, comprising:
a controlled environment defined by a plurality of transparent panels; and
at least one illumination portion that projects light having a wavelength of between 400nm and 550nm and having an irradiance of between 10microWatt/cm2/nm and 35microWatt/cm2/nm, the illumination portion comprising at least one light emitting diode portion that projects the light when energized,
wherein the plurality of transparent panels are contiguous to one another and include a first panel that serves as a substrate for an anode layer and a cathode layer of the at least one illumination portion, the first panel being formed from a transparent material such that the controlled environment is exposed to ambient light through the first panel.

12. The phototherapy device of claim 11, wherein the plurality of transparent panels include at least one opening having at least one glove portion attached thereto such that a user is able to manipulate one or more objects in the controlled environment using the at least one glove portion.

13. The phototherapy device of claim 11, wherein at least one of the plurality of transparent panels is movable so as to provide an opening through which the infant is moved such that an infant is able to be placed in and removed from the controlled environment.

14. The phototherapy device of claim 11, wherein the at least one light emitting diode portion is transparent when not energized such that the controlled environment is exposed to ambient light through the light emitting diode portion.

15. The phototherapy device of claim 11, wherein the plurality of transparent panels include at least:
a top panel,
a bottom panel arranged parallel to the top panel, and
four side panels comprising two long side panels arranged parallel to one another and two short side panels arranged parallel to one another.

16. The phototherapy device of claim 15 wherein the at least one illumination portion is on the top panel.

17. The phototherapy device of claim 11, wherein the illumination portion has a top portion and a bottom portion, wherein at least the bottom portion of the illumination portion projects the light into the controlled environment, wherein the at least one illumination portion is integrated into at least one of the plurality of transparent panels such that at least the bottom portion of the illumination portion is covered by the transparent material.

18. The phototherapy device of claim 11, wherein the illumination portion has a top portion and a bottom portion, wherein at least the bottom portion projects the light onto the controlled environment, wherein the at least one illumination portion is attached to an inner surface of at least one of the plurality of transparent panels surface of the top panel.

19. The phototherapy device of claim 15, wherein the illumination portion comprises two or more light emitting diode portions, wherein at least a first light emitting diode portion is attached to the top panel and at least a second light emitting diode portion is attached to bottom panel.

20. The phototherapy device of claim 11, wherein the at least one light emitting diode portion includes an organic light emitting diode portion.

* * * * *